United States Patent [19]

Douglas et al.

[11] 4,166,860

[45] Sep. 4, 1979

[54] IMIDAZOLE AMIDINOUREAS FOR STIMULATING $H_2$-RECEPTORS

[75] Inventors: George H. Douglas, Malvern; Bernard J. Burns, Philadelphia; Henry F. Campbell, Lansdale, all of Pa.

[73] Assignee: William H. Rorer, Inc., Fort Washington, Pa.

[21] Appl. No.: 840,934

[22] Filed: Oct. 11, 1977

[51] Int. Cl.$^2$ .......................................... A61K 31/415
[52] U.S. Cl. .................................................. 424/273 R
[58] Field of Search ......................... 424/273; 548/342

[56] References Cited

U.S. PATENT DOCUMENTS 3,808,336  4/1974  Durant et al. ..................... 548/342

*Primary Examiner*—Stanley J. Friedman
*Attorney, Agent, or Firm*—James A. Nicholson; John C. Smith, Jr.

[57] ABSTRACT

A method of stimulating histamine $H_2$-receptors in mammals employing imidazole amidinoureas.

8 Claims, No Drawings

IMIDAZOLE AMIDINOUREAS FOR STIMULATING H₂-RECEPTORS

SUMMARY OF THE INVENTION

This invention describes a method of treating mammals with imidazole amidinoureas in order to stimulate histamine H-2 receptors for the treatment of gastrointestinal disorders and diseases.

It has long been postulated that many of the physiologically active substances within the animal body, in the course of their activity, combine with certain specific sites known as receptors. Histamine is a compound which is believed to act in such a way but since the actions of histamine fall into more than one type, it is believed that there is more than one type of histamine receptor. The type of action of histamine which is blocked by drugs commonly called "antihistamines" (of which mepyramine is a typical example) is believed to involve a receptor which has been designated by Ash and Schile (Brit. J. Pharmac. Chemother, 27:427, 1966) as H-1. The substances and pharmaceutical compositions of the present invention are distinguished by the fact that they act at histamine receptors other than the H-1 receptor, that is they act at H-2 histamine receptors which are described by Black et al. Nature 236, 385 (1972), Black et al cited above, page 390, column 2, state the following:

"Mepyramine has been defined as an H₁-receptor antagonist and burimamide has now been defined as an H₂-receptor antagonist. Used alone, burimamide can antagonize those responses to histamine, such as stimulation of acid gastric secretion, which cannot be blocked by mepyramine; histamine apparently activates H₂-receptors to produce these effects."

Thus, from the Black et al paper, H-2 histamine receptors are those histamine receptors which are not inhibited by mepyramine but are inhibited by burimamide. Thus they are of utility in inhibiting certain actions of histamine which are not inhibited by the above mentioned "antihistamines". Agonists of H-2 histamine receptors are useful, for example, as enhancers of histamine activity in the same manner as 4-methylhistamine as described by Levi et al in *Pharmacological Characterization of Cardiac Histamine Receptors: Sensitivity to H₁- and H₂ Receptor Agonists and Antagonists*, European Journal of Pharmacology 30 (1957) 328-335.

The compounds of the present invention may be used in the treatment of gastrointestinal disorders such as achlorhydria. Also, because of the compounds ability to enhance H₂- receptor activity and thus inhibit contractions of the uterus, it can be used in the treatment of dysmenorrhea.

Also the administration of the compounds of this invention can serve as a pharmacological tool in the testing of antihistamine activity. In this respect, it has been found that the compounds of this invention are selective stimulants of histamine H₂-receptors with no side reactions, especially in having no effect on the histamine H₁-receptors. The selectivity is especially important in pharmacological studies of compounds which are intended for use as antihistamines or with respect to the study of the cardiac histamine effects.

DESCRIPTION AND PREFERRED EMBODIMENT

This invention relates to a new method of treating gastrointestinal disorders and diseases, and of gastrointestinal therapeutic compositions, which comprises the utilization of imidazole amidinoureas having the structural formula as shown in Formula I.

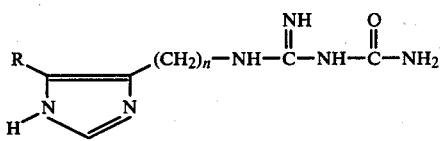

where:
n is 1-3, and
R is hydrogen or lower alkyl.

The term "lower alkyl" refers to an alkyl hydrocarbon group containing from 1 to about 8 carbon atoms which may be straight chained or branched.

It is well known in the pharmacological arts that non-toxic acid addition salts of pharmacologically active amine compounds do not differ in activities from their free base. The salts merely provide a convenient solubility factor.

The amines of this invention may be readily converted to their non-toxic acid addition salts by customary methods in the art. The non-toxic salts of this invention are those salts the acid component of which is pharmacologically acceptable in the intended dosages; such salts would include those prepared from inorganic acids, organic acids, higher fatty acids, high molecular weight acids, etc. and include such as: hydrochloric acid, hydrobromic acid, sulfuric acid, nitric acid, phosphoric acid, methane sulfonic acid, benzenesulfonic acid, acetic acid, propionic acid, malic acid, oxalic acid, succinic acid, glycolic acid, lactic acid, salicylic acid, benzoic acid, nicotinic acid, phthalic acid, stearic acid, oleic acid, abietic acid, etc.

Representative compounds of this invention which are particularly useful are as follows:

1-[(4-imidazolyl)methylamidino]urea
1-[2-(4-imidazolyl)ethylamidino]urea
1-[3-(4-imidazolyl)propylamidino]urea
1-[(5-methyl-4-imidazolyl)methylamidino]urea
1-[2-(5-methyl-4-imidazolyl)ethylamidino]urea
1-[3-(5-methyl-4-imidazolyl)propylamidino]urea
1-[(5-ethyl-4-imidazolyl)methylamidino]urea
1-[2-(5-ethyl-4-imidazolyl)ethylamidino]urea
1-[3-(5-ethyl-4-imidazolyl)propylamidino]urea
1-[(5-propyl-4-imidazolyl)methylamidino]urea
1-[2-(5-propyl-4-imidazolyl)ethylamidino]urea
1-[3-(5-propyl-4-imidazolyl)propylamidino]urea
1-[(5-butyl-4-imidazolyl)methylamidino]urea
1-[2-(5-butyl-4-imidazolyl)ethylamidino]urea
1-[3-(5-butyl-4-imidazolyl)propylamidino]urea
1-[(5-pentyl-4-imidazolyl)methylamidino]urea
1-[2-(5-pentyl-4-imidazolyl)ethylamidino]urea
1-[3-(5-pentyl-4-imidazolyl)propylamidino]urea
1-[(5-hexyl-4-imidazolyl)methylamidino]urea
1-[2-(5-hexyl-4-imidazolyl)ethylamidino]urea
1-[3-(5-hexyl-4-imidazolyl)propylamidino]urea
1-[(5-heptyl-4-imidazolyl)methylamidino]urea
1-[2-(5-heptyl-4-imidazolyl)ethylamidino]urea
1-[3-(5-heptyl-4-imidazolyl)propylamidino]urea
1-[(5-octyl-4-imidazolyl)methylamidino]urea
1-[2-(5-octyl-4-imidazolyl)ethylamidino]urea
1-[3-(5-octyl-4-imidazolyl)propylamidino]urea The compounds of this invention may be prepared by the following general procedures:

Reaction of a substituted [4(5)-imidazolyl] alkylamine with O-m-tolyl-N-cyanoisourea results in the formation of a substituted 1-[4(5)-imidazolyl] alkyl-3-cyanoguanidine. This condensation can be carried out in an inert solvent at raised temperatures. It is preferably carried out in an alcohol such as isopropanol at reflux.

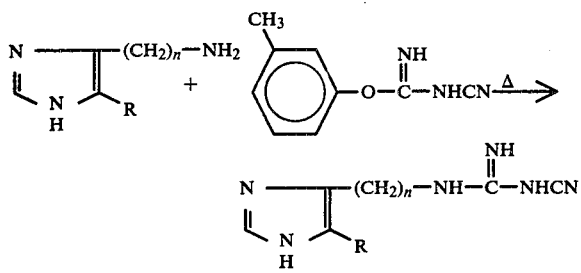

where n=1-3.

The substituted 1-[4(5)-imidazolyl] alkyl-3-cyanoguanidine may also be prepared by condensation of the corresponding substituted [4(5)-imidazolyl] alkyl-amine with sodium dicyanamide. This reaction can be carried out in an inert solvent at raised temperatures.

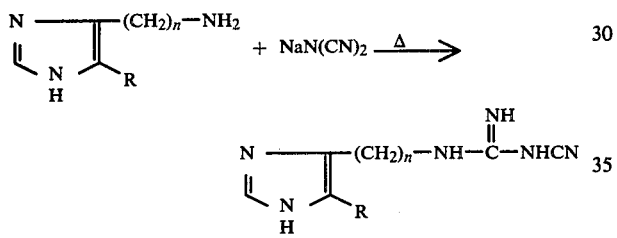

The O-m-tolyl-N-cyanoisourea of the above condensation may be prepared by reacting m-cresol with cyanogenbromide to obtain the m-tolyl cyanate. Treatment with cyanamide results in the O-m-tolyl-N-cyanoisourea.

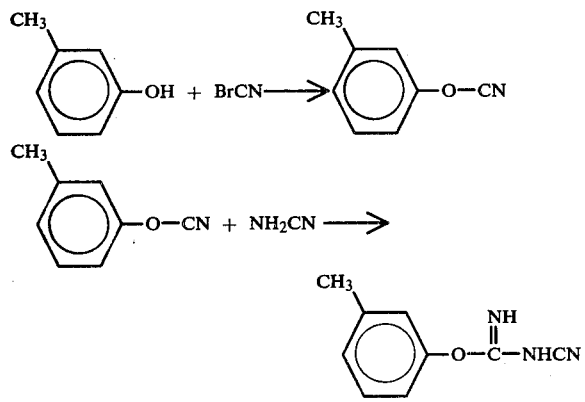

Hydrolysis of a substituted 1-[4-(5)-imidazolyl]alkyl-3-cyanoguanidine with aqueous mineral acid results in the formation of the corresponding substituted 1-[4(5)-imidazolyl]alkyl amidinourea. This reaction is preferably carried out in a polar medium such as alcohol and at temperatures which may range from room temperature to reflux. Isopropanol is a preferred solvent.

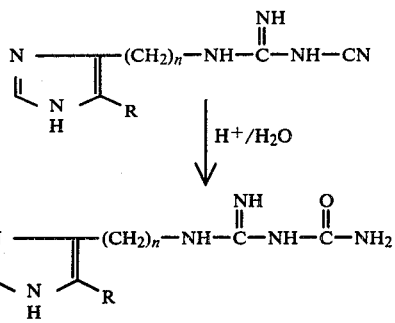

When the starting imidazolylalkylamine material is histamine then condensation with O-m-tolyl-N-cyanoisourea in an inert solvent at raised temperatures results in the formation of 1-(2-[4-(5)-imidazolyl]ethyl)-3-cyanoguanidine. Hydrolysis of the latter in a polar medium with an aqueous mineral acid results in the formation of the 1-(2-[4(5)-imidazolyl]ethylamidino)urea. The latter reaction is preferably carried out in an alcohol such as isopropanol at temperatures ranging from room temperature to reflux.

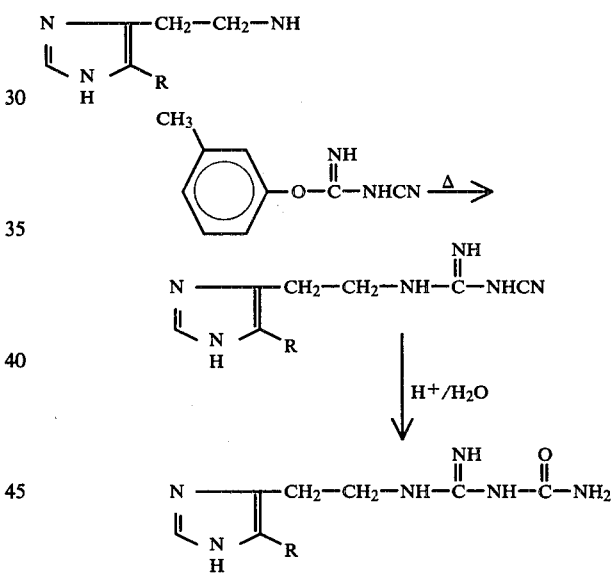

The starting materials of this invention are either known compounds or their method of preparation is described.

We have found that the compounds of this invention have a useful degree of gastric secretory activity and are effective in the treatment of some gastrointestinal disorders. It should further be noted that these compounds are also characterized by their low acute toxicity.

For all these purposes, the compounds of this invention can be normally administered parenterally. The term "parenteral" as used herein, includes subcutaneous injection, intravenous, intramuscular or intrasternal injection or infusion techniques.

The pharmaceutical compositions may be in the form of a sterile injectable preparation, for example, as a sterile injectable aqueous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example, as an aqueous solution buffered to a pH of 4.0 to 7.0 and made isotonic with sodium chloride.

Further, these compounds may be formulated so that for every 100 parts by weight of the compositions, there are present between 5 and 95 parts by weight of the active ingredient. The dosage unit form will generally contain between about 1 mg. and about 500 mg. of the active ingredients of this invention. The preferred unit dose is between about 10 mg. and about 100 mg.

The dosage regimen in carrying out the methods of this invention is that which insures maximum therapeutic response until improvement is obtained and thereafter the minimum effective level which gives relief. Thus, in general, the dosages are those that are therapeutically effective in the treatment of gastrointestinal disease conditions or symptoms. In general, the daily dose can be between about 0.5 mg/kg and 70 mg/kg (preferably in the range of 2-25 mg/kg/day), bearing in mind, of course, that in selecting the appropriate dosage in any specific case, consideration must be given to the patient's weight, general health, age and other factors which may influence response to the drug.

The following are detailed Examples which show the preparation of the compounds of this invention. They are to be construed as illustrations of said compounds and not as limitations thereof.

EXAMPLE I

A. N-cyano-N'-[(5-methyl-4-imidazolyl)methyl]guanidine 5.16 g. (0.0280 mole) 5-methyl-4-(aminomethyl)imidazole dihydrochloride is converted to the free base with $K_2CO_3$. A solid free base is taken up in 70 ml. isopropyl alcohol. 4.90 g. (0.0280 mole) O-m-tolyl-N-cyanoisourea is added, heated 30 minutes to reflux, then refluxed for one hour. The mixture is then cooled, and a small amount of the white solid is filtered off. The filtrate is then stripped to give a solid-cresol mixture, triturated in benzene, and filtered. The collected solid is recrystallized from $MeOH/CH_3CN$ to obtain N-cyano-N'-[(5-methyl-4-imidazolyl)methyl] guanidine having a m.p. of 216°-221° C.

B. 1-[(5-methyl-4-imidazolyl)methylamidino]urea dihydrochloride 1.80 g. (0.0101 mole) N-cyano-N'-[(5-methyl-4-imidazolyl) methyl] guanidine is taken up in 100 ml. isopropanol. 2.5 ml. conc. HCl is added. The reaction mixture is then heated for 20 minutes to reflux and refluxed for 65 minutes to obtain complete hydrolysis. The mixture is then cooled and filtered. The material is then recrystallized from $MeOH/CH_3CN$ to obtain 1-[(5-methyl-4-imidazolyl)methylamidino]urea dihydrochloride with a m.p. of 214°-214.5° C.

EXAMPLE II

A. N-cyano-N'-[(4-imidazolyl)methyl]guanidine.

5.48 g. (0.0322 mole) 4-aminomethylimidazole dihydrochloride is converted to the free base using $Na_2CO_3$. The solid base is combined with 5.64 g. (0.0322 mole) O-m-tolyl-N-cyanoisourea in 82 ml. isopropanol. This mixture is then heated for 15 minutes to reflux, and refluxed for one hour. The mixture is then cooled to room temperature, filtered to remove cloudiness, and stripped to obtain a cloudy oil of cresol mixed with the product.

B. 1-[(4-imidazolyl)methylamidino]urea dihydrochloride

A cresol-cyanoguanidine mixture is taken up in 322 ml. isopropanol. 15.8 ml. conc. HCl is added, heated 18 minutes to reflux, and refluxed for 30 minutes. The reaction mixture is then cooled in ice and refrigerated overnight. The mixture is then filtered, and a yellowish solid is collected. The mixture is recrystallized from $MeOH/CH_3CH$, to obtain 1-(4-imidazolyl)methylamidino]urea dihydrochloride with a m.p. of 203.5°-204.5° C.

EXAMPLE III

A. N-cyano-N'-[2-(4-imidazolyl)ethyl]guanidine 3.62 g. histamine (0.0300 mole) and 5.26 g. (0.0300 mole) O-m-tolyl-N-cyanoisourea are combined in 75 ml. of isopropanol. The mixture is heated 25 minutes to reflux and refluxed 70 minutes. The reaction solution is cooled and stripped to a light orange oil, triturated in benzene, decanted, and the residue is recrystallized from $MeOH/CH_3CN$ to obtain N-cyano-N'-[2-(4-imidazolyl)ethyl] guanidine having a m.p. of 152°-154° C.

B. 1-[2-(4-imidazolyl)ethylamidino]urea dihydrochloride 47.5 g. histamine (0.401 mole) and 71.66 g. (0.409 mole) O-m-tolyl-N-cyanoisourea are combined in 500 ml. of isopropanol. The mixture is then heated for 10 minutes to reflux, refluxed for one hour, and the reaction mixture is stripped to an oil. The oil is taken up in 2 l. of isopropanol and 102 ml. conc. HCl, heated 25 minutes to reflux, refluxed for 35 minutes, cooled slowly, then with ice. The mixture is filtered to obtain 1-[2-(4-imidazolyl)ethylamidino]urea dihydrochloride as a crude product. This is recrystallized from $MeOH/CH_3CN$ to obtain 1-[2-(4-imidazolyl)ethylamidino]urea dihydrochloride with a m.p. of 180.5°-181.5° C.

EXAMPLE IV

A. N-cyano-N'-[2-(5-methyl-4-imidazolyl)ethyl] guanidine 4.94 g. (0.249 mole) 5-methyl-4-(2-aminoethyl) imidazole dihydrochloride is converted to the free base with NaOH. The free base is combined with 4.36 g. (0.0249 mole) of O-m-tolyl-N-cyanoisourea in 63 ml. isopropanol. This mixture is refluxed for one hour. The mixture is then cooled to room temperature, filtered to remove insoluble material, and the solvent is evaporated to obtain a cloudy oil of the product mixed with m-cresol.

B. 1-[2-(5-methyl-4-imidazolyl)ethylamidino]urea dihydrochloride

A cresol-cyanoguanidine mixture is taken up in 225 ml. isopropanol, 6.3 m. conc. HCl is added, and this reaction mixture is heated to reflux over 10 minutes and refluxed for one hour. The isopropanol is evaporated and the resulting residue is cooled in an ice-bath, filtered and washed with isopropanol/ethylacetate to give crude product. This material is recrystallized from $MeOH/CH_3CN$ to give 1-[2-(5-methyl-4-imidazolyl)e- thylamidino]urea dihydrochloride, having a m.p. of 205.5° C.

EXAMPLE V

A. N-cyano-N'-[3-(4-imidazolyl)propyl] guanidine 6.2 g. (0.031 mole) of 4-(3-aminopropyl)imidazole dihydrochloride is converted to the free base using NaOH. The free base is combined with 5.4 g. (0.031 mole) of O-m-tolyl-N-cyanoisourea in 100 ml. isopropanol. This mixture is refluxed for 3 hours. The mixture is then cooled to room temperature, filtered to remove insoluble material and the solvent is evaporated to obtain a cloudy oil of the product mixed with m-cresol.

B. 1-[3-(4-imidazolyl)propylamidino]urea dioxalate monohydrate

A cresol-cyanoguanidine mixture is taken up in 300 ml. isopropanol, 8.5 ml. conc. HCl is added, and this reaction mixture is heated to reflux over 20 minutes and refluxed for 30 minutes. The isopropanol is evaporated leaving behind an oily residue. The crude dihyrochloride is converted to the free base using NaOH. The dioxalate salt is prepared from isopropanol to obtain 1-[3-(4-imidazolyl)propylamidino]urea dioxalate monohydrate with a m.p. of 60°–70° C.

EXAMPLE VI

When the procedures of Examples I–V are followed, by substituting the starting materials for those below, then the corresponding product is obtained:

| STARTING MATERIAL | PRODUCT |
| --- | --- |
| 5-methyl-4-(3-aminopropyl) imidazole dihydrochloride | 1-[3-(5-methyl-4-imidazolyl) propylamidino]urea |
| 5-ethyl-4-(aminomethyl) imidazole dihydrochloride | 1-[(5-ethyl-4-imidazolyl) methylamidino]urea |
| 5-ethyl-4-(2-aminoethyl) imidazole dihydrochloride | 1-[2-(5-ethyl-4-imidazolyl) ethylamidino]urea |
| 5-ethyl-4-(3-aminopropyl) imidazole dihydrochloride | 1-[3-(5-ethyl-4-imidazolyl) propylamidino]urea |
| 5-propyl-4-(aminomethyl) imidazole dihydrochloride | 1-[(5-propyl-4-imidazolyl) methylamidino]urea |
| 5-propyl-4-(2-aminoethyl) imidazole dihydrochloride | 1-[2-(5-propyl-4-imidazolyl) ethylamidino]urea |
| 5-propyl-4-(3-aminopropyl) imidazole dihydrochloride | 1-[3-(5-propyl-4-amidazolyl) propylamidino]urea |
| 5-butyl-4-(aminomethyl) imidazole dihydrochloride | 1-[(5-butyl-4-imidazolyl methylamidino]urea |
| 5-butyl-4-(2-aminoethyl) imidazole dihydrochloride | 1-[2-(5-butyl-4-imidazolyl) ethylamidino]urea |
| 5-butyl-4-(3-aminopropyl) imidazole dihydrochloride | 1-[3-(5-butyl-4-imidazolyl) propylamidino]urea |
| 5-pentyl-4-(aminomethyl) imidazole dihydrochloride | 1-[(5-pentyl-4-imidazolyl) methylamidino]urea |
| 5-pentyl-4-(2-aminoethyl) imidazole dihydrochloride | 1-[2-(5-pentyl-4-imidazolyl) ethylamidino]urea |
| 5-pentyl-4-(3-aminopropyl) imidazole dihydrochloride | 1-[3-(5-pentyl-4-imidazolyl) propylamidino]urea |
| 5-hexyl-4-(aminomethyl) imidazole dihydrochloride | 1-[(5-hexyl-4-imidazolyl) methylamidino]urea |
| 5-hexyl-4-(2-aminoethyl) imidazole dihydrochloride | 1-[2-(5-hexyl-4-imidazolyl) ethylamidino]urea |
| 5-hexyl-4-(3-aminopropyl) imidazole dihydrochloride | 1-[3-(5-hexyl-4-imidazolyl) propylamidino]urea |
| 5-heptyl-4-(aminomethyl) imidazole dihydrochloride | 1-[5-heptyl-4-imidazolyl) methylamidino]urea |
| 5-heptyl-4-(2-aminoethyl) imidazole dihydrochloride | 1-[2-(5-heptyl-4-imidazolyl) ethylamidino]urea |
| 5-heptyl-4-(3-aminopropyl) imidazole dihydrochloride | 1-[3-(5-heptyl-4-imidazolyl) propylamidino]urea |
| 5-octyl-4-(aminomethyl) imidazole dihydrochloride | 1-[(5-octyl-4-imidazolyl) methylamidino]urea |
| 5-octyl-4-(2-aminoethyl) imidazole dihydrochloride | 1-[2-(5-octyl-4-imidazolyl) ethylamidino]urea |
| 5-octyl-4-(3-aminopropyl) imidazole dihydrochloride | 1-[3-(5-octyl-4-imidazolyl) propylamidino]urea |

EXAMPLE VII

Five hundred ampoules each with 2 ml. of solution which contain 15 mg. of 1-[(5-methyl-4-imidazolyl)methylamidino]urea dihydrochloride is prepared from the following types and amounts of materials:

| Ingredient | Grams |
| --- | --- |
| 1-[(5-methyl-4-imidazolyl) methylamidino]urea dihydrochloride | 7.5 |
| Ascorbic Acid | 1.0 |
| Sodium bisulphite | 0.5 |
| Sodium sulphite | 1.0 |

The previous ingredients are added to distilled water, diluted to 1 liter of solution and thoroughly mixed. The solution is used to fill ampoules which are sterilized hot in the usual way.

We claim:

1. A method of stimulating histamine $H_2$-receptors in mammals which comprises administering parenterally thereto between 0.5 mg/kg-70 mg/kg per day of a compound of the formula

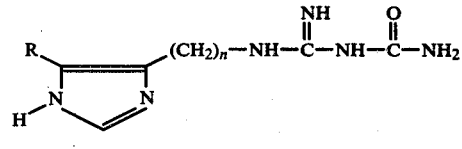

where:
 n is 1–3 and
 R is hydrogen or lower alkyl; and a non-toxic acid addition salt thereof.

2. The method of claim 1 wherein the compound is 1-[(5-methyl-4-imidazolyl)methylamidino]urea.

3. The method of claim 1 wherein the compound is 1-[(4-imidazolyl)methylamidino]urea.

4. The method of claim 1 wherein the compound is 1-[2-(4-imidazolyl)ethylamidino]urea.

5. The method of claim 1 wherein the compound is 1-[2-(5-methyl-4-imidazolyl)ethylamidino]urea.

6. The method of claim 1 wherein the compound is 1-[3-(4-imidazolyl)propylamidino]urea.

7. The method of claim 1, wherein said compound is administered for the treatment of achlorhydria.

8. The method of claim 1 wherein said compound is administered for the treatment of dysmenorrhea.

* * * * *